US00PP26813P3

(12) United States Plant Patent
Hammett

(10) Patent No.: US PP26,813 P3
(45) Date of Patent: Jun. 7, 2016

(54) ***COSMOS* PLANT NAMED 'HAMCOEC'**

(50) Latin Name: *Cosmos hybrida*
Varietal Denomination: Hamcoec

(71) Applicant: Keith Richard William Hammett, Auckland (NZ)

(72) Inventor: Keith Richard William Hammett, Auckland (NZ)

(73) Assignee: Kiwiflora Ltd., Kaiwaka (NZ)

( * ) Notice: Subject to any disclaimer, the term of this patent is extended or adjusted under 35 U.S.C. 154(b) by 129 days.

(21) Appl. No.: 14/121,126

(22) Filed: Aug. 4, 2014

(65) Prior Publication Data

US 2015/0082502 P1 Mar. 19, 2015

(30) Foreign Application Priority Data

Sep. 17, 2013 (NZ) ..... PBR 31608

(51) Int. Cl.
*A01H 5/02* (2006.01)

(52) U.S. Cl.
USPC ..... Plt./418
CPC ..... *A01H 5/025* (2013.01)

(58) Field of Classification Search
USPC ..... Plt./418
CPC ..... A01H 5/025
See application file for complete search history.

*Primary Examiner* — Kent L Bell

(57) ABSTRACT

A new cultivar of *Cosmos* plant named 'Hamcoec' that is characterized by large diameter red-brown inflorescences with yellow pollen, large ray florets and long peduncles.

1 Drawing Sheet

Botanical classification: *Cosmos hybrida.*
Variety denomination: 'Hamcoec'.

CROSS-REFERENCE TO RELATED AND CO-PENDING APPLICATIONS

This application claims the benefit of priority under 35 U.S.C. 119(f) of the application for a grant of New Zealand Plant Breeders Rights which was filed for the instant plant variety on Sep. 17, 2013, Application Number 31608.

BACKGROUND OF THE INVENTION

The present invention relates to a new and distinct cultivar of *Cosmos* plant botanically known as *Cosmos hybrida* and hereinafter referred to by the cultivar name 'Hamcoec'.

'Hamcoec' originated from open pollination of the female or seed parent plant an unidentified proprietary *Cosmos atrosanguineus* (not patented). The male or pollen parent plant is unknown. The resulting seeds were subsequently harvested and grown. 'Hamcoec' was selected as a single plant from within the stated progeny in a controlled environment in Auckland, New Zealand in 2009.

Asexual reproduction of the new cultivar 'Hamcoec' first occurred by tissue culture in 2009 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Cosmos* cultivar 'Hamcoec'. These traits in combination distinguish 'Hamcoec' as a new and distinct cultivar apart from other existing known varieties of *Cosmos.*

1. *Cosmos* 'Hamcoec' exhibits large diameter red-brown inflorescences with yellow pollen.
2. *Cosmos* 'Hamcoec' exhibits inflorescences having large ray florets.
3. *Cosmos* 'Hamcoec' exhibits long peduncles.

The closest comparison cultivar is *Cosmos* 'Coco Mocha' (not patented). 'Hamcoec' is distinguishable from 'Coco Mocha' by the following characteristics:

1. 'Hamcoec' exhibits leaves that have fewer divisions than the leaves of 'Coco Mocha'.
2. 'Hamcoec' exhibits larger diameter inflorescences than the inflorescences of 'Coco Mocha'.
3. 'Hamcoec' exhibits longer peduncles than the peduncles of 'Coco Mocha'.
4. 'Hamcoec' exhibits longer, broader and flatter ray florets than the ray florets of 'Coco Mocha'. The ray florets of 'Coco Mocha' are smaller and incurved.

In comparison to the female or seed parent plant. an unidentified proprietary *Cosmos atrosanguineus*, 'Hamcoec' is distinguishable by the following characteristics:

1. 'Hamcoec' exhibits darker color red-brown inflorescences than the inflorescences of the seed parent plant.
2. 'Hamcoec' exhibits smaller diameter inflorescences than the inflorescences of the seed parent plant.

BRIEF DESCRIPTION OF THE DRAWING

The accompanying photograph illustrates the distinguishing traits of *Cosmos* 'Hamcoec'. The plants in the photograph show an overall view of a 3 month old plant grown outdoors in Auckland, New Zealand.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Cosmos* cultivar named 'Hamcoec'. Data was collected in Auckland, New Zealand from 3 month old outdoor grown plants. The time of year was Summer in the Southern Hemisphere and the temperature range was 18-25 degrees Centigrade during the day and 6-12 degrees Centigrade at night. The light level was natural outdoor light. Color determinations are in accordance with The Royal Horticultural Society Colour Chart 2007 edition, except where general color terms of ordinary dictionary significance are used. The growing requirements are similar to the species. 'Hamcoec' has not been tested under all possible conditions and phenotypic differences may be observed with variations in environmental, climatic, and cultural conditions, however, without any variance in genotype.

Botanical classification: *Cosmos hybrida* 'Hamcoec'.

Use: Ornamental perennial.

Parentage: 'Hamcoec' originated from open pollination of the female or seed parent plant an unidentified proprietary *Cosmos atrosanguineus.*

Vigor: High.

Low temperature tolerance: USDA zone 9.

Propagation: Tissue culture.

Crop time: 7 weeks to produce a 4.5 inch container.

Root system: Fine and fibrous.

Growth habit: Upright and outwardly spreading.

Overall height: 80.2 cm.

Overall width: 67.0 cm.

Stem:

*Stem shape.*—Cylindrical.

*Stem dimensions.*—0.6 cm. in diameter and 23.4 cm. in length.

*Stem texture.*—Slightly pubescent.

*Stem color.*—144C and 144D.

*Internode length.*—8.1 cm.

Foliage:

*Leaf arrangement.*—Opposite.

*Compound or single.*—Single.

*Quantity of leaves per plant.*—220.

*Texture.*—Smooth (both surfaces).

*Leaf shape.*—Pinnate.

*Leaf apex.*—Acute.

*Leaf base.*—Acuminate.

*Leaf margin.*—Entire.

*Leaf length.*—9.8 cm.

*Leaf width.*—8.6 cm.

*Young leaf color* (*lower surface*).—137C.

*Young leaf color* (*upper surface*).—In between 137B and N137B.

*Mature leaf color* (*lower surface*).—147B.

*Mature leaf color* (*upper surface*).—N137B.

*Vein color* (*under surface*).—147C.

*Vein color* (*upper surface*).—146B to 146C.

*Venation pattern.*—Pinnate.

*Leaf attachment.*—Petiolate.

Petiole:

*Petiole dimensions.*—0.35 cm. in width, 0.25 cm. in height and 7.8 cm. in length.

*Petiole color.*—152B, margins N137C.

Inflorescence:

*Inflorescence arrangement.*—Capitulum.

*Natural flowering season.*—Spring through Summer.

*Fragrance.*—Slight chocolate scent.

*Inflorescence size.*—4.1 cm. in diameter, 1.8 cm. in height.

*Quantity of inflorescences per plant.*—75.

*Inflorescence bud length.*—1.0 cm.

*Inflorescence bud diameter.*—1.0 cm.

*Bud shape.*—Globose.

*Bud color.*—In between N186C and 200A.

Ray florets:

*Arrangement.*—Single outer circle.

*Shape.*—Obovate.

*Dimensions.*—2.1 cm. in length and 1.3 cm. in width.

*Apex.*—Truncate.

*Base.*—Obtuse.

*Margin.*—Entire.

*Texture* (*both surfaces*).—Puberulous.

*Quantity of ray florets per flower.*—8.

*Color* (*lower surface*).—In between N186C and 187A.

*Color* (*upper surface*).—In between 59A and 187A.

Disc florets:

*Arrangement.*—Circular.

*Shape.*—Tubular.

*Dimensions.*—1.3 cm. in length and 0.3 cm. in width.

*Apex.*—Divergent stigmas.

*Base.*—Subtended from receptacle.

*Margin.*—Entire.

*Texture* (*both surfaces*).—Smooth.

*Quantity of disc florets per inflorescence.*—40.

*Color* (*both surfaces*).—Both surfaces in between N186C and 187A, middle section of both surfaces 174C, base 150D.

Peduncle:

*Peduncle dimensions.*—44.5 cm. in length and 0.3 cm. in width.

*Peduncle angle.*—0° (straight on top of lateral branch).

*Peduncle color.*—199A and 152A.

*Peduncle strength.*—Moderate.

Reproductive organs:

*Androecium.*—Present on disc florets only.

*Anther shape.*—Cylindrical.

*Anther length.*—0.4 cm.

*Anther color.*—203A.

*Filament length.*—0.5 cm.

*Amount of pollen.*—High.

*Pollen color.*—15A.

*Gynoecium.*—Present on disc florets only.

*Pistil length.*—1.0 cm.

*Stigma shape.*—Divergent bifid curved.

*Stigma color.*—187A.

*Style length.*—0.8 cm.

*Style color.*—187A.

*Ovary dimensions.*—0.3 cm. in length and 0.075 cm. in width.

*Ovary color.*—157D.

Fruit and seed production has not been observed.

Disease and pest resistance: Plants of the new cultivar have not been observed for disease and pest resistance.

The invention claimed is:

1. A new and distinct variety of *Cosmos* plant named 'Hamcoec' as described and illustrated.

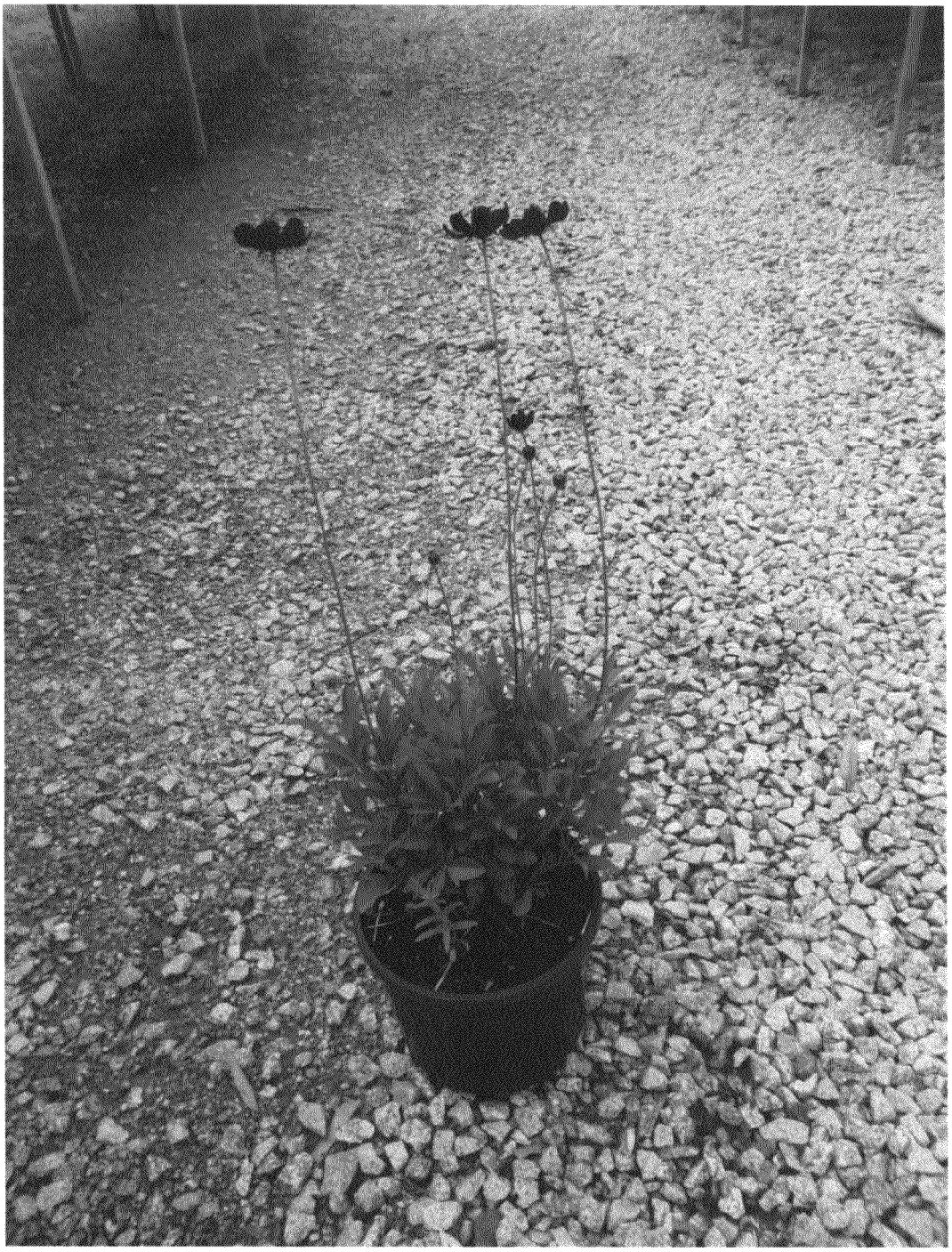

* * * * *